(12) United States Patent
Spenciner

(10) Patent No.: US 11,839,546 B2
(45) Date of Patent: Dec. 12, 2023

(54) MECHANICAL FUSE FOR SURGICAL IMPLANTS AND RELATED METHODS

(71) Applicant: Medos International Sarl, Le Locle (CH)

(72) Inventor: David B. Spenciner, North Attleboro, MA (US)

(73) Assignee: Medos International Sarl, Le Locle (CH)

( * ) Notice: Subject to any disclaimer, the term of this patent is extended or adjusted under 35 U.S.C. 154(b) by 163 days.

(21) Appl. No.: 17/476,449

(22) Filed: Sep. 15, 2021

(65) Prior Publication Data

US 2022/0000623 A1    Jan. 6, 2022

Related U.S. Application Data

(62) Division of application No. 15/960,165, filed on Apr. 23, 2018, now Pat. No. 11,135,066.

(51) Int. Cl.
| | | |
|---|---|---|
| *A61F 2/30* | (2006.01) | |
| *A61B 5/103* | (2006.01) | |
| *A61B 90/00* | (2016.01) | |
| *A61B 5/00* | (2006.01) | |

(52) U.S. Cl.
CPC .............. *A61F 2/30* (2013.01); *A61B 5/1036* (2013.01); *A61B 90/06* (2016.02); *A61B 5/4504* (2013.01); *A61B 5/4528* (2013.01); *A61B 2090/064* (2016.02); *A61F 2002/30461* (2013.01);

(Continued)

(58) Field of Classification Search
CPC ... A61B 5/1036; A61B 5/4504; A61B 5/4528; A61B 2090/064; A61F 2002/30461; A61F 2002/30558; A61F 2002/30561; A61F 2/30

See application file for complete search history.

(56) References Cited

U.S. PATENT DOCUMENTS

| | | |
|---|---|---|
| 4,858,620 A | 8/1989 | Sugarman et al. |
| 6,034,296 A | 3/2000 | Elvin et al. |
| 6,245,109 B1 | 6/2001 | Mendes et al. |

(Continued)

OTHER PUBLICATIONS

U.S. Appl. No. 15/960,165, filed Apr. 23, 2018, Mechanical Fuse for Surgical Implants and Related Methods.

(Continued)

*Primary Examiner* — Robert A Lynch
*Assistant Examiner* — Mikail A Mannan

(57) ABSTRACT

Devices and methods for tissue and graft procedures are provided that are designed to fail under a certain amount of force, providing sensory feedback that a particular activity may be providing too much stress on a surgical implant. For example, a surgical implant can include a sacrificial element in the form of a filament designed to break when a certain threshold value of force is met or exceeded, while a second filament that has the ability to withstand higher values of force, is able to maintain the repair after the first filament fails. In other embodiments, the sacrificial element includes a filament engagement mechanism associated with a suture anchor configured to fail at a threshold value of force, and a second filament engagement mechanism of the anchor can maintain the repair after the first one fails. Many implants configurations are provided, as are various surgical methods incorporating sacrificial elements.

4 Claims, 8 Drawing Sheets

(52) U.S. Cl.
CPC ............... *A61F 2002/30558* (2013.01); *A61F 2002/30561* (2013.01)

(56) References Cited

U.S. PATENT DOCUMENTS

| | | | |
|---|---|---|---|
| 6,447,425 B1 | 9/2002 | Keller et al. |
| 6,447,448 B1 | 9/2002 | Ishikawa et al. |
| 6,610,096 B2 | 8/2003 | MacDonald |
| 7,097,662 B2 | 8/2006 | Evans, III et al. |
| 7,878,988 B2 | 2/2011 | Bush et al. |
| 7,918,887 B2 | 4/2011 | Roche |
| 8,070,695 B2 | 12/2011 | Gupta et al. |
| 8,083,741 B2 | 12/2011 | Morgan et al. |
| 8,372,147 B2 | 2/2013 | Roche |
| 8,372,153 B2 | 2/2013 | Roche |
| 8,425,616 B2 | 4/2013 | Clifford et al. |
| 8,486,070 B2 | 7/2013 | Morgan et al. |
| 8,551,092 B2 | 10/2013 | Morgan et al. |
| 8,687,865 B2 | 4/2014 | Wilson et al. |
| 8,721,643 B2 | 5/2014 | Morgan et al. |
| 8,790,278 B2 | 7/2014 | Walter et al. |
| 8,814,905 B2 | 8/2014 | Sengun et al. |
| 8,821,543 B2 | 9/2014 | Hernandez et al. |
| 8,894,684 B2 | 11/2014 | Sengun |
| 8,915,132 B1 | 12/2014 | Ward |
| 9,060,763 B2 | 6/2015 | Sengun |
| 9,095,331 B2 | 8/2015 | Hernandez et al. |
| 9,198,750 B2 | 12/2015 | Van Kampen et al. |
| 9,345,468 B2 | 5/2016 | Sengun et al. |
| 9,757,113 B2 | 9/2017 | Pasquali et al. |
| 9,763,655 B2 | 9/2017 | Sengun |
| 9,888,998 B2 | 2/2018 | Sengun et al. |
| 11,135,066 B2 | 10/2021 | Spenciner |
| 2013/0013005 A1* | 1/2013 | Ferree .............. A61B 17/06061 606/328 |
| 2014/0194907 A1 | 7/2014 | Bonutti et al. |
| 2014/0228880 A1 | 8/2014 | Bisson et al. |
| 2014/0257346 A1 | 9/2014 | Sengun et al. |
| 2014/0343350 A1 | 11/2014 | Martinson et al. |
| 2014/0364771 A1 | 12/2014 | Pitts et al. |
| 2015/0157449 A1 | 6/2015 | Gustafson et al. |
| 2016/0157851 A1 | 6/2016 | Spenciner |
| 2016/0361155 A1 | 12/2016 | Van Kampen |
| 2017/0215864 A1 | 8/2017 | Sengun et al. |
| 2019/0321182 A1 | 10/2019 | Spenciner |

OTHER PUBLICATIONS

Burkhart, S. S., "Superior Capsular Reconstruction (SCR), Surgical Technique," (Video); Arthrex, Inc., Ref. #: VID1-00875-EN; Version A, Revision date Jan. 12, 2017; <https://www.arthrex.com/resources/video/RUuuuWAwqkW3qwFZkvER6g/superior-capsular-reconstruction-scr#share-assetvideo-modal >.

Heinzelman, A.D., et al., "A Combined Technique for Distal Biceps Repair Using a Soft Tissue Button and Biotenodesis Interference Screw," Amer. J. Sports Med., 2009, v. 37, pp. 989-994.

* cited by examiner

MECHANICAL FUSE FOR SURGICAL IMPLANTS AND RELATED METHODS

CROSS REFERENCE TO RELATED APPLICATIONS

The present application is a divisional of and claims priority to U.S. patent application Ser. No. 15/960,165, filed Apr. 23, 2018, and entitled "MECHANICAL FUSE FOR SURGICAL IMPLANTS AND RELATED METHODS," the contents of which are hereby incorporated by reference herein.

FIELD

The present disclosure relates to devices, systems, and methods for securing a soft tissue graft to bone, and more particularly relates to surgical implants that include a sacrificial element (sometimes referred to herein as a "mechanical fuse") configured to proactively break and thereby produce sensory feedback in response to an applied load of the graft exceeding a threshold while the tissue graft repair remains intact. The sensory feedback in the form of a sound and/or uneasy feeling can serve as a warning to the patient to avoid certain movements or physical activity.

BACKGROUND

Joint injuries may commonly result in the complete or partial detachment of ligaments, tendons, and soft tissues from bone. Tissue detachment may occur in many ways, e.g., as the result of an accident such as a fall, overexertion during a work related activity, during the course of an athletic event, or in any one of many other situations and/or activities. These types of injuries are generally the result of excess stress or extraordinary forces being placed upon the tissues.

In the case of a partial detachment, commonly referred to under the general term "sprain," the injury frequently heals without medical intervention, the patient rests, and care is taken not to expose the injury to undue strenuous activities during the healing process. If, however, the ligament or tendon is completely detached from its attachment site on an associated bone or bones, or if it is severed as the result of a traumatic injury, surgical intervention may be necessary to restore full (or close to full) function to the injured joint. A number of conventional surgical procedures exist for re-attaching tendons, ligaments or other soft tissue to bone.

One example is the knee 100 shown in FIG. 1, which includes anterior and posterior cruciate ligaments 102, 104 extending from the head of the tibia 106 to the intercondylar notch of the femur 108. These ligaments operate to prevent forward and backward relative motion between the two bones. When ruptured (e.g., as can happen in strenuous athletic movements), surgical reconstruction can be necessary.

Tears in the cruciate ligaments of the knee can be repaired using a ligament graft taken from a cadaver (i.e., an allograft) or from a patient's own tissue (i.e., an autograft). Reconstruction procedures generally involve forming a hole in both the femur and tibia, and then securing opposite ends of the ligament graft in these holes. In one cruciate ligament repair procedure, a ligament graft is associated with a surgical implant and secured to the femur. A common femoral fixation means includes an elongate body, sometimes referred to as a cortical button or "button." The cortical button is attached to a suture loop that is sized to allow an adequate length of a soft tissue graft to lie within the femoral tunnel while providing secure extra-cortical fixation.

Another surgical procedure may involve arthroscopic knot tying, which is commonly practiced in shoulder rotator cuff and instability procedures. Typically, an anchor loaded with suture is first attached to bone. The suture is normally slidably attached to the anchor through an eyelet or around a post, such that a single length of suture has two free limbs. One limb of the suture is passed through soft tissue to be repaired such as a tendon or labrum. The two ends of the suture are then tied to each other, thereby capturing the soft tissue in a loop with the anchor. Upon tightening the loop, the soft tissue is approximated to the bone via the anchor.

As with any surgical procedure, a repaired tendon, ligament, or other soft tissue needs time to heal. However, it is not uncommon for a patient to start feeling better relatively soon after the repair or reconstruction procedure. If a patient attempts to resume rigorous physical activity too soon after the procedure and/or the patient is too aggressive in performing their post-operative rehabilitation, there is a risk that the repair of the tendon, ligament, or other soft tissue may fail. For example, the suture loop can post-operatively loosen, slip, and/or break, causing the tissue graft to move away from the desired location.

Accordingly, there is a need for improved surgical implants and methods for use in repair and reconstruction procedures that produce post-operative sensory feedback in response to patient movements or other activity that may cause potential failure of a repaired tendon, ligament or other soft tissue.

SUMMARY

The present disclosure provides for surgical implants, and methods of using the same, having a sacrificial element, also referred to as a mechanical fuse, designed to fail at a certain threshold value of force to provide sensory feedback that an action causing a force that meets or exceeds the certain threshold value is likely providing force that is detrimental to the surgical implant The sacrificial element is designed to break or otherwise fail to indicate that the threshold value has been met or exceeded, and then the portion of the implant, or tissue or graft associated with the same, can be maintained by a nearby component of the implant that is designed to capture the object that had previously been associated with the sacrificial element to prevent total failure of the implant. The nearby component typically has a higher threshold value than the sacrificial element so it does not fail under similar circumstances. In some instances the sacrificial element includes a sacrificial filament (or other similar component or equivalent, as discussed herein) that is designed to hold a graft, tissue, or the like with respect to an implantable body, and when the sacrificial filament fails, a second filament associated with the implantable body, referred to herein as a repair filament, is configured to receive the graft, tissue, or the like that was being held by the implantable body. In some other instances the sacrificial element includes a sacrificial suture engagement mechanism that is part of a suture anchor. The sacrificial suture engagement mechanism is designed to maintain a repair filament coupled to the suture anchor, with the repair filament being used in a repair procedure, such as for capturing and drawing tissue towards bone as part of a soft tissue repair. When the sacrificial suture engagement mechanism fails due to the application of a force by the repair filament that meets or exceeds the threshold value of the sacrificial suture engagement mechanism, a filament engagement mechanism that is also part of the suture anchor can be designed to capture the repair filament so that the repair filament remains close to its original location with respect to the suture anchor when the repair had been completed.

One exemplary embodiment of a surgical implant includes an implantable body, a repair filament, and a sacrificial element. The implantable body has at least one passageway extending at least partially through the body. The repair filament is disposed in the at least one passageway, and forms a repair loop configured to connect the implantable body and a tissue. The repair filament has a first maximum load-bearing capacity. The sacrificial element is associated with the implantable body and/or the sacrificial element. The sacrificial element is configured to carry an applied load of the repair filament and/or the tissue, and has a second maximum load-bearing capacity. The second maximum load-bearing capacity is lower than the first maximum load-bearing capacity of the repair filament such that the sacrificial element is configured to produce sensory feedback in response to the applied load of the repair filament and/or the tissue exceeding the second maximum load-bearing capacity.

In some embodiments, the sacrificial element can include a sacrificial filament. In some such embodiments, the at least one passageway can include at least two passageways, with each passageway extending between a proximal end and a distal end of the implantable body. Further, each of the repair filament and the sacrificial filament can extend through each of the at least two passageways such that each of the repair filament and the sacrificial filament is disposed above a top side of the implantable body and below a bottom side of the implantable body, the top and bottom sides being opposed to each other. The sacrificial filament can form a sacrificial loop configured to produce the sensory feedback in response to an applied load from the tissue when the applied load exceeds the second maximum load-bearing capacity of the sacrificial filament. In some such embodiments, the sensory feedback can be associated with the sacrificial loop breaking in response to the applied load from the tissue when the applied load exceeds the second maximum load-bearing capacity of the sacrificial filament. Alternatively, or additionally, a circumference formed by the sacrificial loop can be smaller than a circumference formed by the repair loop. In some embodiments that include a sacrificial filament, the second maximum load-bearing capacity of the sacrificial filament can be approximately one half of the first maximum load-bearing capacity of the repair filament.

A number of other configurations involving a sacrificial filament are also provided. For example, the sacrificial filament can be configured to form a sacrificial loop disposed approximately transverse to the repair loop, with the sacrificial loop constricting opposing sides of the repair loop at a location between the implantable body and a distal end of the repair loop. In some such embodiments, the sensory feedback can be associated with the sacrificial loop breaking in response to the opposing sides of the repair loop stretching the sacrificial loop until the second maximum load-bearing capacity of the sacrificial filament is exceeded.

By way of further non-limiting example, the sacrificial filament can be configured to form one or more sacrificial stitches that can connect opposing sides of the repair loop at a location between the implantable body and a distal end of the repair loop. In some such embodiments, the sensory feedback can be associated with at least one sacrificial stitch of the one or more sacrificial stitches breaking in response to the opposing sides of the repair loop stretching the at least one sacrificial stitch until the second maximum load-bearing capacity of the sacrificial filament is exceeded.

By way of still further non-limiting example, the sacrificial filament can be integrated with (or otherwise associated with, as provided for herein) the repair filament to form a sacrificial loop integrated with the repair loop. In some such embodiments, the sensory feedback can be associated with the sacrificial loop breaking while the repair loop remains intact in response to the tissue applying a load greater than the second maximum load-bearing capacity of the sacrificial filament and less than the first maximum load-bearing capacity of the repair filament.

Alternatively, or additionally, the sacrificial element can include a sacrificial weld that connects opposing sides of the repair loop at a location between the implantable body and a distal end of the repair loop. In some such embodiments, the sensory feedback can be associated with the sacrificial weld breaking in response to the opposing sides of the load-bearing loop stretching the sacrificial weld until the second maximum load-bearing capacity of the sacrificial weld is exceeded.

In some other embodiments, the implantable body can include a suture anchor and the sacrificial element can include an element that is part of the suture anchor. Such embodiments can further include a sacrificial element that includes a sacrificial filament, while other such embodiments may not include a sacrificial element that includes a sacrificial filament. More particularly, the suture anchor can include both a filament engagement mechanism and the sacrificial element that includes a sacrificial filament engagement mechanism. In some such embodiments, the sacrificial filament engagement mechanism can be distally spaced apart from the filament engagement mechanism, with a second maximum load-bearing capacity of the sacrificial filament engagement mechanism being lower than a maximum load-bearing capacity of the filament engagement mechanism. Further, the repair filament can be disposed at least partially around each of the filament engagement mechanism and the sacrificial filament engagement mechanism, with a distal-most portion of the repair filament being engaged with the sacrificial filament engagement mechanism. The sensory feedback can be associated with the sacrificial filament engagement mechanism breaking in response to the repair filament applying a force against the sacrificial filament engagement mechanism that exceeds the second maximum load-bearing capacity of the sacrificial filament engagement mechanism.

An exemplary method of using a surgical implant that includes a sacrificial element includes performing a tissue repair procedure that results in an implantable body being disposed at a surgical location site, with the implantable body having a repair filament coupled to it, and a sacrificial element associated with the implantable body. The tissue repair procedure results in tissue being disposed at a desired location with respect to bone in the body. The sacrificial element is configured to carry an applied load of at least one of the repair filament and the tissue. The repair filament has a first maximum load-bearing capacity, and the sacrificial element has a second maximum load-bearing capacity that is lower than the first maximum load-bearing capacity of the repair filament. Further, the sacrificial element is configured to produce sensory feedback in response to the applied load of the respective tissue and the repair filament exceeding the second maximum load-bearing capacity of the sacrificial element after the tissue repair procedure has been completed. As discussed in greater detail below, the sacrificial element can take a variety of forms, including but not limited to a sacrificial filament and a suture engagement mechanism that is part of a suture anchor. Likewise, the tissue can be tissue in the body and/or a graft.

In some embodiments, the sacrificial element can include a sacrificial filament coupled to the implantable body and the tissue can include a graft. In some such embodiments, the action of performing a tissue repair procedure can include coupling the graft to the sacrificial filament. The sacrificial filament can be configured to produce the sensory feedback in response to the applied load of the graft to the sacrificial filament exceeding the second maximum load-bearing capacity of the sacrificial filament. For example, the sensory feedback can be the sacrificial filament breaking. In some such embodiments, the sacrificial filament can include a sacrificial loop and the action of coupling the graft to the sacrificial filament can include disposing the graft within the sacrificial loop such that the graft is in contact with the sacrificial loop.

In some other embodiments, the sacrificial element can include a sacrificial filament that is associated with the repair filament, the repair filament can include a repair loop, and the tissue can include a graft. In some such embodiments, the action of performing a tissue repair procedure can include coupling the graft to the repair filament. The sacrificial filament can be configured to produce the sensory feedback in response to opposing sides of the repair loop stretching the sacrificial filament until the second maximum load-bearing capacity of the sacrificial filament is exceeded. In some such embodiments, the sacrificial filament can include a sacrificial loop disposed approximately transverse to the repair loop such that the sacrificial loop constricts opposing sides of the repair loop at a location between the implantable body and a distal end of the repair filament. Alternatively, or additionally, the sacrificial filament can include one or more sacrificial stitches that connect opposing sides of the repair loop.

In still some other embodiments, the sacrificial element can include a sacrificial filament integrated with (or otherwise associated with, as provided for herein) the repair filament, with the sacrificial filament forming a sacrificial loop and the repair filament forming a repair loop. The sacrificial loop and the repair loop can also be integrated to form an integrated loop, and the tissue can include a graft. In some such embodiments, the action of performing a tissue repair procedure can include disposing the graft within the integrated loop with the graft being in contact with the integrated loop. The sacrificial loop can be configured to produce the sensory feedback in response to the applied load of the graft exceeding the second maximum load-bearing capacity of the sacrificial loop such that the sacrificial loop breaks while the repair loop remains intact, thus allowing the graft to remain disposed within the repair loop after the sacrificial loop breaks.

In yet some other embodiments, the repair filament can include a repair loop, the sacrificial element can include a sacrificial weld that connects opposing sides of the repair loop, and the tissue can include a graft. In some such embodiments, the action of performing a tissue repair procedure can include disposing the graft within the repair loop. The sacrificial weld can be configured to produce the sensory feedback in response to the opposing sides of the repair loop stretching the sacrificial weld until the second maximum load-bearing capacity of the sacrificial filament is exceeded.

The sacrificial element can also be something other than a sacrificial filament. For example, the sacrificial element can be part of the implantable body. In such embodiments, a sacrificial filament may or may not also be used in conjunction with the sacrificial element that is part of the implantable body. In some embodiments, the implantable body can include a suture anchor that includes both the sacrificial element and a filament engagement mechanism. The sacrificial element can include a sacrificial filament engagement mechanism, and the repair filament can be coupled to the sacrificial filament engagement mechanism. In some such embodiments, the action of performing a tissue repair procedure can include disposing the implantable body in bone, coupling the repair filament to tissue, and advancing the tissue towards the bone in which the implantable body is disposed. The sacrificial filament engagement mechanism can be configured to produce the sensory feedback in response to the applied load of the repair filament to the sacrificial filament engagement mechanism exceeding the second maximum load-bearing capacity of the sacrificial filament engagement mechanism.

BRIEF DESCRIPTION OF THE DRAWINGS

The accompanying drawings, which are incorporated herein and constitute part of this specification, illustrate exemplary embodiments, and together with the background and summary given above and the detailed description given below, serve to explain the features of the various embodiments. The drawings include.

DETAILED DESCRIPTION

Figure 1:
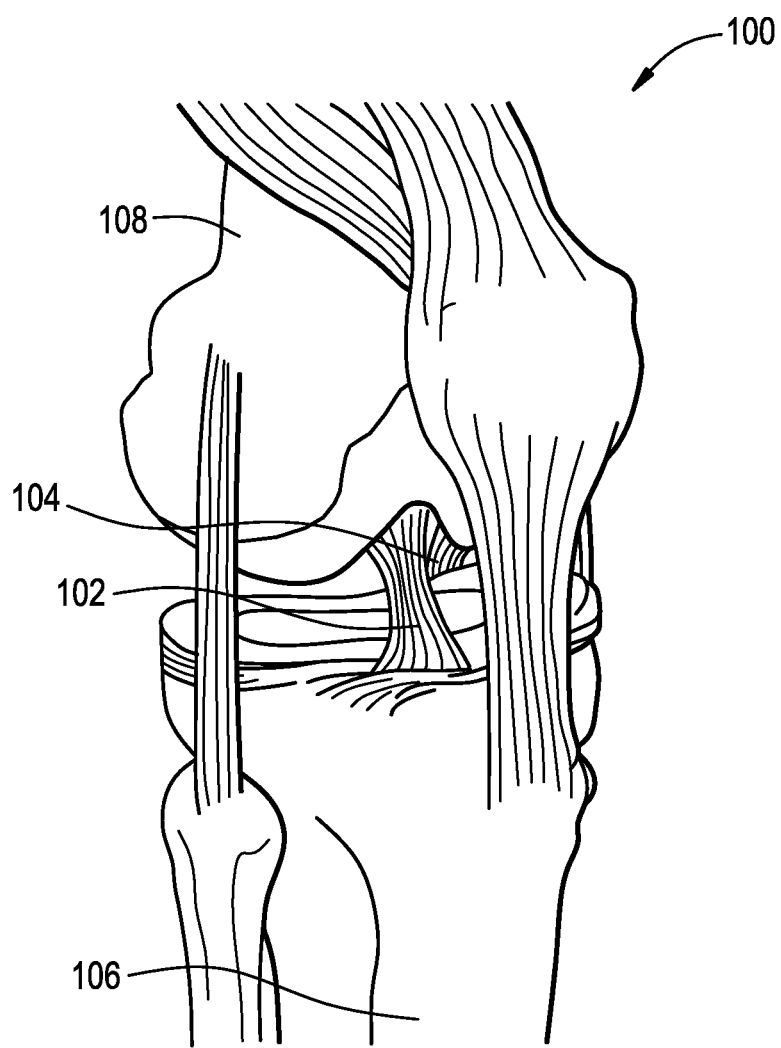
FIG. 1 illustrates the anatomy of a human knee.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure. Sizes and shapes of the devices, and the components thereof, can depend on a variety of factors, including but not limited to an anatomy and tendencies of the subject (i.e., patient) in which the devices will be used, the size and shape of components with which the devices will be used, the methods and procedures in which the devices will be used, and the preferences of the surgeon operating the devices and/or otherwise performing the related procedure(s).

In the present disclosure, like-numbered and/or like-named (e.g., sacrificial filament, sacrificial loop, sacrificial stitch, sacrificial weld, etc.) components of the embodiments generally have similar features and/or purposes, unless stated otherwise. To the extent arrows are used to describe a direction a component can be tensioned or pulled, these arrows are illustrative and in no way limit the direction the respective component can be tension or pulled. A person skilled in the art will recognize other ways and directions for creating the desired tension or movement. Likewise, while in some embodiments movement of one component is described with respect to another, a person skilled in the art will recognize that other movements are possible. To the extent features or steps are described herein as being a "first feature," "first loop," or "first step," or a "second feature," "second loop," or "second step," such numerical ordering is generally arbitrary, and thus such numbering can be interchangeable. Additionally, a number of terms may be used throughout the disclosure interchangeably but will be understood by a person skilled in the art. By way of non-limiting example, the terms "suture" and "filament" may be used interchangeably, and in some instances, simultaneously. Further, use of a term like "tissue" may encompass a variety of materials, including but not limited to ligaments, tendons, grafts, and/or other soft tissue disposed in the body.

The present disclosure generally relates to surgical implants for use in reconstructive procedures such as tendon, ligaments, or other soft tissue repairs that includes an implantable body, a repair filament coupled to the implantable body, and a sacrificial element, also referred to as a mechanical fuse, associated with one or both of the implantable body and the repair filament. In some embodiments, the implantable body can be a cortical button, a suture anchor, or other tissue graft fixation devices. The repair filament can be configured to form one or more repair loops or other repair constructs for connecting the implantable body to a tissue graft. The sacrificial element that is at the heart of the present disclosure can take a variety of forms, including but not limited to a sacrificial filament and a sacrificial filament engagement mechanism (e.g., saddle, post), among other sacrificial constructs that are provided for herein or are otherwise derivable from the present disclosures. The sacrificial element is configured to have a lower load-bearing capacity than the repair filament so that the sacrificial element breaks proactively in response to an applied load of a tissue graft exceeding a threshold that does not break the repair filament or any other part of the repair mechanism. When the sacrificial element breaks, the patient may hear, feel or otherwise experience sensory feedback, e.g., a popping sound and/or an uneasy feeling or sensation. Because the sacrificial element is configured to break at lower loads than the repair filament, the repair filament can remain intact when the sacrificial element breaks, such that the tissue graft repair is maintained. Accordingly, the sensory feedback produced by the sacrificial element breaking can serve as warning to the patient to avoid certain movements or physical activity or risk failure of the tissue graft repair. The warning may also cause patients to seek out medical attention or advice.

Figure 2:
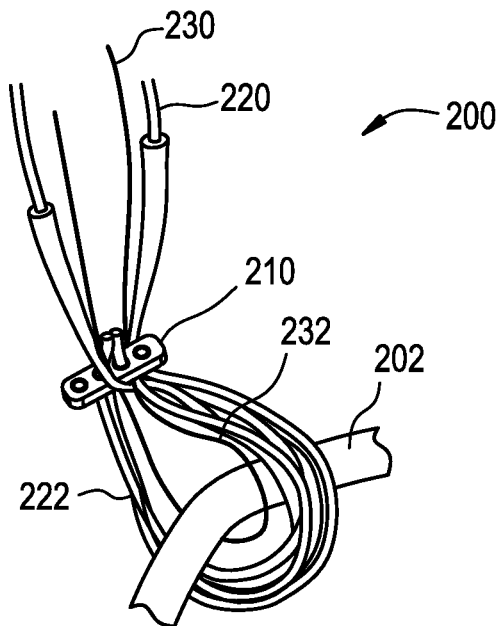
FIG. 2 is a perspective view of one exemplary embodiment of a surgical implant that includes a cortical button, a repair filament forming an outer repair loop, and a sacrificial filament forming an inner sacrificial loop.

FIG. 2 is a perspective view of one exemplary embodiment of a surgical implant 200 that includes a sacrificial element. In the illustrated embodiment, the surgical implant 200 includes a cortical button or implant body 210, a repair filament 220, and a sacrificial filament 230, also referred to as a mechanical fuse. The repair filament 220 can be configured to form one or more outer repair loops 222 and the sacrificial filament 230 can be configured to form one or more inner sacrificial loops 232 such that each loop has a proximal end coupled to the cortical button 210 and a distal end surrounding a ligament, tendon, or other soft tissue graft 202. The repair loop 222 and the sacrificial loop 232 can be formed using any known technique for securing a tissue graft to bone using one or more loops of suture filament coupled to a cortical button or other implantable body. Such techniques can include, but are not limited to, the techniques disclosed in U.S. Pat. Nos. 9,757,113, 9,888,998, U.S. Patent Application Publication No. 2014/0257346, U.S. Patent Application Publication No. 2015/0157449, and U.S. Patent Application Publication No. 2016/0157851, the contents of each which is incorporated by reference herein in its entirety. The above-referenced disclosures incorporated by reference are primarily directed to a variety of cortical button configurations, all of which can be used in conjunction with the disclosures provided for herein related to sacrificial elements. As also provided for herein, other types of implantable bodies, including but not limited many different varieties of bone or suture anchors, can likewise be used in conjunction with the disclosures provided for herein related to sacrificial elements.

Figure 3A:
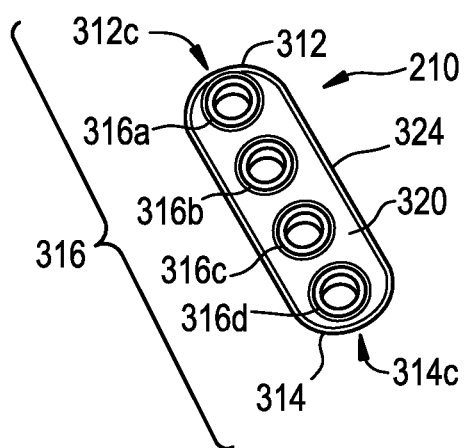
FIG. 3A is a top perspective view of the cortical button of FIG. 2.
Figure 3B:
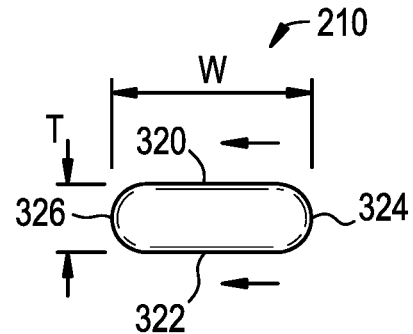
FIG. 3B is an end elevational view of the cortical button of FIG. 3A.
Figure 3C:
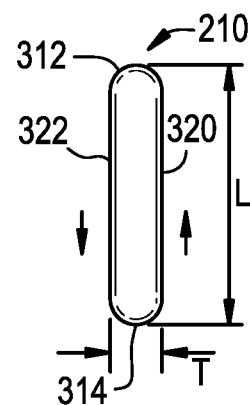
FIG. 3C is a side elevational view of the cortical button of FIG. 3A.

A cortical button 210 for use as a part of a surgical implant to fixate a soft tissue graft in bone is illustrated in FIGS. 3A-3C. The button 210 can have a somewhat rectangular, elongate shape with curved leading and trailing terminal ends 312, 314. Multiple thru-holes or passageways 316 can extend from a first, top surface 320 and through a second, bottom surface 322. In the illustrated embodiment there are two outer thru-holes 316a, 316d disposed, respectively, adjacent to leading and trailing terminal ends 312, 314, and two inner thru-holes 316b, 316c disposed between the two outer holes 316a, 316d. As shown, the outer and inner thru-holes 316a, 316d and 316b, 316c have diameters that are substantially the same, and a space separating adjacent thru-holes 316 is substantially the same for each adjacent pair. A width W of the button 210 is defined by the distance between the two elongate sidewalls 324, 326, as shown in FIG. 3B, a length L of the button 210 is defined by the distance between central portions 312c, 314c of the end walls of the leading and trailing terminal ends 312, 314, as shown in FIG. 3C, and a thickness T of the button 210 is defined by the distance between the top and bottom surfaces 320, 322, as shown in FIGS. 3B and 3C.

In one exemplary embodiment of the substantially rectangular button, the length L of the body of the cortical button is in the range of about 5 millimeters to about 30 millimeters, the width W is in the range of about 1 millimeter to about 10 millimeters, and the thickness T is in the range of about 0.25 millimeters to about 3 millimeters. In one exemplary embodiment, the length L can be about 12 millimeters, the width W can be about 4 millimeters, and the thickness T can be about 1.5 millimeters. Diameters of the thru-holes 324 can be in the range of about 0.5 millimeters to about 5 millimeters, and in one exemplary embodiment each can be about 2 millimeters.

Although in the illustrated embodiment each of the thru-holes 316a, 316b, 316c, 316d has a substantially similar diameter, in other embodiments some of the thru-holes can have different diameters. Additionally, any number of thru-holes can be formed in the button 210, including as few as two. In exemplary embodiments the button 210 can be made from a stainless steel or titanium, but any number of polymers, metals, or other biocompatible materials in general can be used to form the body. Some non-limiting examples of biocompatible materials suitable for forming the body include a polyether ether ketone (PEEK), bioabsorbable elastomers, copolymers such as polylactic acid-polyglycolic acid (PLA-PGA), and bioabsorbable polymers such as polylactic acid. The button 210 can also be formed of absorbable and non-absorbable materials.

A person skilled in the art will recognize that the cortical button 210 described herein is merely one example of a button or other implantable body that can be used in conjunction with the teachings provided herein. A button or other implantable body configured to be associated with suture filaments of the type described herein can have a variety of different shapes, sizes, and features, and can be made of a variety of different materials, depending, at least in part, on the other components with which it is used, such as the suture filament and the soft tissue graft, and the type of procedure in which it is used. Thus, while in the present embodiment the button 210 is somewhat rectangular having curved ends, in other embodiments the body can be substantially tubular, among other shapes. The various configurations of cortical buttons incorporated by reference above are just some non-limiting examples of possible cortical button configurations and set-ups that can be adapted to include or otherwise be used with one or more sacrificial elements.

Each of the repair filament 220 and the sacrificial filament 230 can be an elongate filament, and a variety of different types of suture filaments can be used, including but not limited to a cannulated filament, a braided filament, more broadly an integrated filament (e.g., any manufactured integration or combination of two or more filaments or filament limbs), and a mono filament. Further, the elongate filament need not be a suture, as in some instances the elongate filament can be a tape or other elongate repair construct known to those skilled in the art. The type, size, and strength of the respective filaments 220, 230 can depend, at least in part, on the other materials of the implant, including the material(s) of the cortical button and the graft, tissue, bone, and related tunnels through which they will be passed, the type of procedure in which they are used, the anatomy and tendencies of the patient, and the preferences of the surgeon, among other factors. The amount and type of bioabsorbable material, if any, utilized in the filaments of the present disclosure may likewise be a matter of surgeon preference for the particular surgical procedure to be performed, based, at least in part, on the anatomy and tendencies of the patient.

Figure 4A:
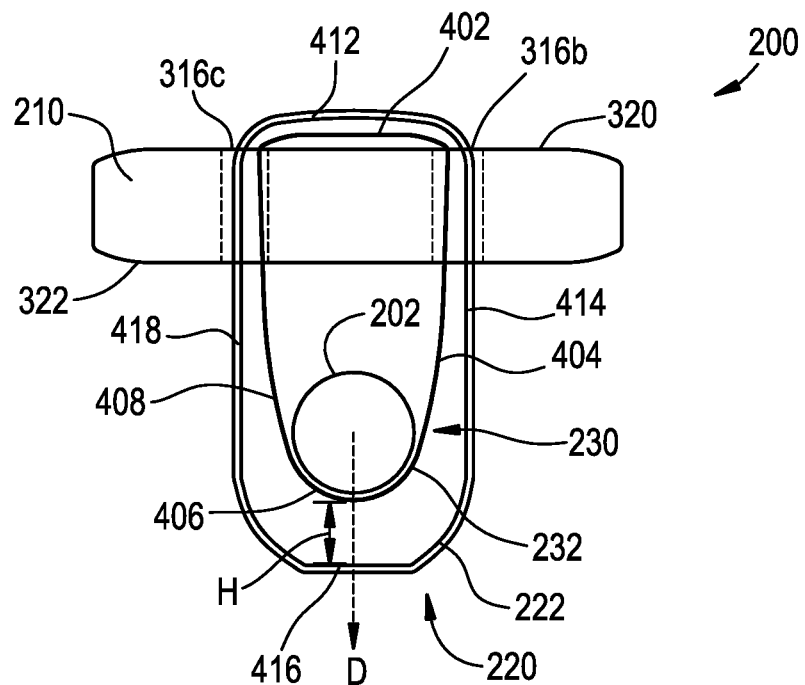
FIG. 4A illustrates a schematic cross-sectional side view of the surgical implant of FIG. 2 when the inner sacrificial loop is intact.
Figure 4B:
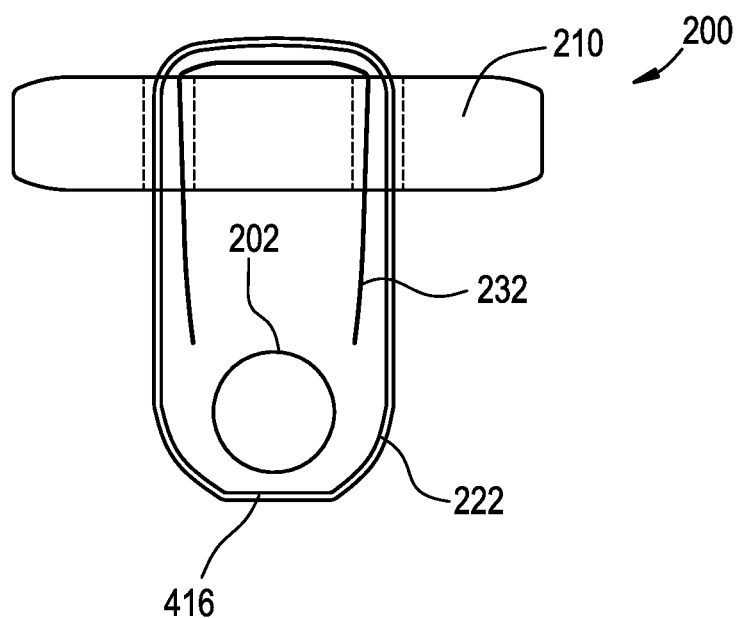
FIG. 4B illustrates a schematic cross-sectional side view of the surgical implant of FIG. 4A when the inner sacrificial loop is broken.

As illustrated in FIGS. 4A and 4B, the sacrificial filament 230 can be configured to have a lower load-bearing capacity than the repair filament 220 so that the sacrificial loop 232 proactively breaks in response to an applied load of a tissue graft exceeding a threshold that does not break the repair loop 222 or button 210. When the inner sacrificial loop 232 breaks, the patient may hear, feel, or otherwise experience sensory feedback in the form of a popping sound and/or an uneasy feeling or sensation. Because the sacrificial filament 230 breaks at lower loads than the repair filament 220, the repair loop 222 can remain intact when the sacrificial loop 232 breaks and thereby maintain the attachment of the cortical button 210 and the tissue graft 202. Accordingly, the sensory feedback associated with the sacrificial filament can serve as warning to the patient to avoid certain movements or physical activity that can cause the tissue graft repair to fail. The warning may also cause patients to seek out medical attention or advice.

FIG. 4A illustrates a schematic cross-sectional side view of the surgical implant of FIG. 2 with the inner sacrificial loop 232 intact. As shown, the inner sacrificial loop 232 can include a proximal end 402 formed by extending the sacrificial filament 230 along a top surface 320 of the cortical button 210, a first side leg 404 formed by the sacrificial filament 230 extending from the top surface 320 through a first thru-hole 316b towards the tissue graft 202, a distal end 406 formed by the sacrificial filament 230 extending around a distal surface of the tissue graft 202, and a second side leg 408 formed by the sacrificial filament 230 extending from the tissue graft 202 to the bottom surface 322 of the button and through a second thru-hole 316c to complete the loop. A person skilled in the art will recognize other terminology that may be appropriate to use to describe the various portions of the loop 232, or other loops provided for herein (e.g., the repair loop 222), and thus usage of terms like proximal and distal end and legs throughout the present application are by no means limiting.

The repair loop 222 forms an outer loop around the inner sacrificial loop 232 and the tissue graft 202. For example, in the illustrated embodiment, the repair loop 222 can include a proximal end 412 formed by the repair filament 220 extending along a top surface 320 of the cortical button 210, a first side leg 414 formed by the repair filament 220 extending from the top surface 320 through the first thru-hole 316b towards the tissue graft 202, a distal end 416 formed by the repair filament 220 extending around the distal end 406 of the inner sacrificial loop 232, and a second side leg 418 formed by the repair filament 220 extending from the tissue graft 202 to the bottom surface 322 of the button and through the second thru-hole 316c to complete the loop.

In some embodiments, the inner sacrificial loop 232 can have a smaller circumference than the circumference of the outer repair loop 222. The smaller circumference of the inner sacrificial loop 232 can form a gap H between the respective distal ends 406, 416 of the sacrificial loop and the repair loop. For example, as shown in FIG. 4B, when the sacrificial loop 232 breaks, the tissue graft 202 can be released distally through the gap until captured by the distal end of the outer repair loop 222, and thereby cause the patient to feel or sense a slight movement of the tissue graft 202. The height of the gap H can be sized so that patient can sense the movement of the tissue graft 202 when the sacrificial loop breaks, but does not compromise the integrity of the repair itself. In some embodiments, the height of the gap can be approximately in the range between about 0.1 mm and about 1 mm.

The sacrificial filament 230 is configured to have a maximum load-bearing capacity that is lower than the maximum load-bearing capacity of the repair filament 220. The respective load-bearing capacities of the repair filament 220 and the sacrificial filament 230 can be defined as the maximum stress (e.g., force) or strain (e.g., deformation) that the respective filament can stand without breaking, rupturing, or otherwise failing. For example, when the tissue graft 202 pulls in a direction away from the cortical button 210, in a direction D, the graft exerts a force on the distal end 406 of the sacrificial loop 232 that causes the loop to stretch. Once the applied force of the tissue graft 202 exceeds the maximum load-bearing capacity of the sacrificial filament 230, the sacrificial loop 232 breaks. This can also be referred to as a threshold force, which is the minimum amount of force that can be applied to the sacrificial filament to cause it to break. Forces greater than the threshold force may also cause the sacrificial filament to break, while forces less than the threshold force are not, at least alone, large enough to cause the sacrificial filament to break.

Because the sacrificial filament 230 is configured to break at loads that do not break the repair filament 220, the sacrificial loop 232 can break while the repair loop 222 remains intact and thereby maintain the attachment between the cortical button 210 and the tissue graft 202. In some embodiments, the sacrificial filament 230 can be configured to have a lower maximum load-bearing capacity by using a filament material having a modulus of elasticity that is less than the modulus of elasticity of the repair filament 220. Additionally or alternatively, the sacrificial filament 230 can be configured to have a lower maximum load-bearing capacity by using a sacrificial filament having a diameter or thickness that is smaller than the diameter or thickness of the repair filament 220. A person skilled in the art, in view of the present disclosures, will understand other properties of the sacrificial and repair filaments that can be different so as to allow the sacrificial filament to break while the repair filament remains impact, including but not limited to the type of material used to make the two filaments and/or the configurations of the two filaments (e.g., braided vs. not braided). Such teachings related to how to achieve different maximum load-bearing capacities and/or threshold force values for repair filaments/loops and sacrificial filaments/loops are applicable to each of the embodiments provided for herein (e.g., FIGS. 5A and 5B, 6A and 6B, 7A and 7B, and 8A and 8B).

When the sacrificial loop 232 breaks, the patient may hear, feel, or otherwise experience some form of sensory feedback. For example, in some embodiments, the sensory feedback may be a sound (e.g., a popping sound) from the sacrificial loop breaking. In some embodiments, the patient may feel a slight movement of the tissue graft 202 in response to the graft being released from the inner sacrificial loop 232 to the outer repair loop 222, the movement resulting from the graft becoming engaged with the outer repair loop 222. Thus, the sensory feedback associated with the sacrificial loop 232 breaking can serve as a warning that the patient's physical activity or movements may risk failure of the tissue graft repair.

Although the illustrated embodiment provides for a single sacrificial loop 232, a person skilled in the art will appreciate that the sacrificial loop 232 can include a plurality of loops, just as the repair loop 222 can include a plurality of loops. Thus, the term "loop" is not limited to a single loop, and can include a plurality of loops. In instances in which the sacrificial loop 232 includes a plurality of loops, the loops can have similar threshold forces such that the loops are configured to break at about the same force value, or they can have graduated threshold forces such that different loops are configured to break at different force values. In an instance in which the loops having different threshold force values, a first loop may be configured to break at a first threshold force and a second loop may be configured to break at a second threshold force, with the second threshold force being greater than the first threshold force. This can allow for multiple warnings or triggers to be communicated to the subject based on the amount of force applied to the sacrificial loop 232.

Figure 5A:
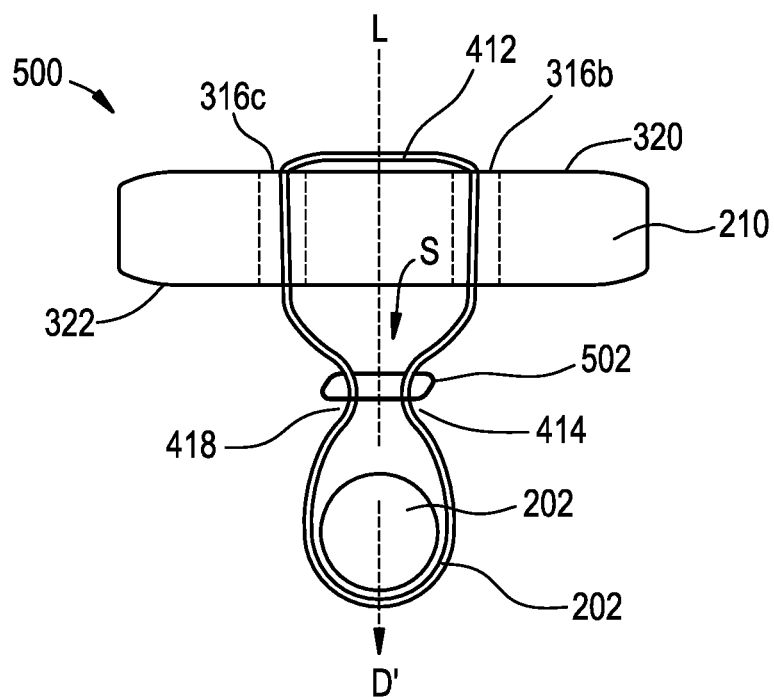
FIG. 5A illustrates a schematic cross-sectional side view of one exemplary embodiment of a surgical implant that includes a cortical button, a repair loop, and a sacrificial loop disposed transversely to the repair loop.
Figure 5B:
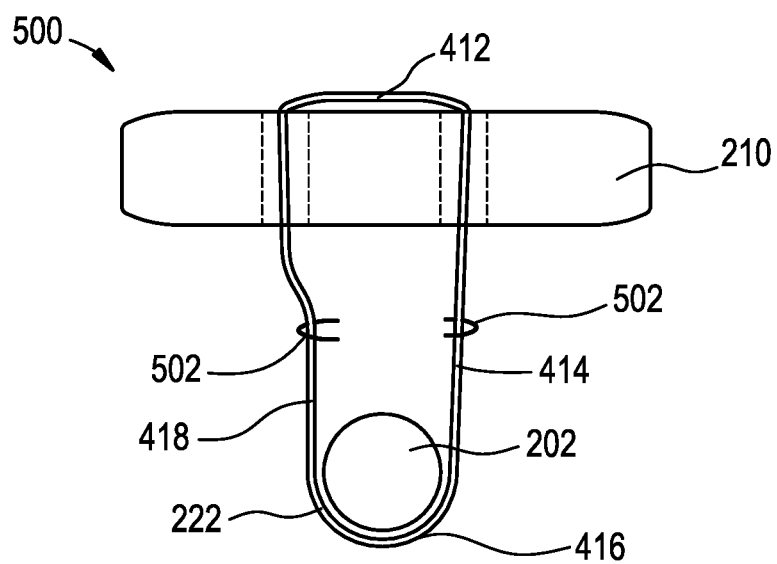
FIG. 5B illustrates a schematic cross-sectional side view of the surgical implant of FIG. 5A when the transversely disposed sacrificial loop is broken.

The present disclosure also provides for a variety of non-limiting examples of sacrificial filament configurations. By way of example, FIGS. 5A and 5B illustrate a sacrificial filament that includes a sacrificial loop 502 associated with the repair loop 222. As shown, a surgical implant 500 includes the cortical button or body 210, the repair loop 222, and the sacrificial loop 502 disposed transversely to the repair loop 222. In the illustrated embodiment of FIG. 5A, the repair loop 222 can include the proximal end 412 extending along the top surface 320 of the cortical button 210, the first side leg 414 extending from the top surface 320 through the first thru-hole 316b towards the tissue graft 202, the distal end 416 extending around the distal surface of the tissue graft 202, and the second side leg 418 extending from the tissue graft 202 to the bottom surface 322 of the button and through the second thru-hole 316c to complete the loop.

As shown, the sacrificial loop 502 is associated with the repair loop 222. More particularly, the sacrificial loop 502 can be associated with the repair loop 222 at a location between the bottom surface 322 of the cortical button 210 and a proximal surface of the tissue graft 202 captured within the repair loop 222. Further, the sacrificial loop 502 can be disposed approximately transverse to the repair loop 222 such that the sacrificial loop 502 is approximately perpendicular to a longitudinal axis L extending approximately centrally through the implant 500. The longitudinal axis L is substantially parallel to a length of the thru-holes 316b and 316c of the body 210 (and thus longitudinal axes thereof, which are not drawn, but understood by a person skilled in the art) and disposed approximately centrally therebetween. The sacrificial loop 502 can be configured to have a circumference or width that constricts the opposing side legs 414 and 418 of the repair loop 422. Although in the illustrated embodiment a single sacrificial loop 502 is shown, in other instances the sacrificial loop 502 can include a plurality of loops. Thus, reference to a "loop" is by no means limiting to a single loop. In other embodiments, the sacrificial loop 502 can include a plurality of loops.

The sacrificial loop 502 can be formed in a variety of ways. By way of non-limiting example, in some embodiments the sacrificial loop 502 can be formed by tying terminal portions of the sacrificial filament around the opposing side legs 414 and 418 of the repair loop 222 until the circumference of the sacrificial loop 502 constricts the legs a desired amount. A person skilled in the art will recognize many other ways by which the sacrificial loop can be formed, including but not limited to tying terminal portions of the sacrificial filament together to form the sacrificial loop that can constrict the desired amount, or the sacrificial loop being pre-formed as a continuous loop having a size that can constrict the desired amount, or the sacrificial loop including one or more connectors that can hold one portion of the sacrificial filament used to form the loop 502 with respect to another portion of filament, thereby forming the sacrificial loop. In some instances, a kit can be provided having different types of sacrificial elements, including sacrificial loops that provide varying levels of constriction.

The desired amount of constriction can be defined by an amount of space S disposed between the opposing side legs 414, 418 of the repair loop 222. The space S is smaller than a space would exist between the side legs 414, 418 if no sacrificial element was associated with the repair loop 222. In some instances, it may be desirable for there to be no space therebetween such that the legs 414 and 418 are in contact at a location at which the sacrificial loop 502 is disposed. In other instances, such as the instance illustrated in FIG. 5A, the legs 414 and 418 are constricted by the sacrificial loop 502 without touching, having the space S, sometimes referred to as a gap, disposed therebetween.

The sacrificial loop 502 can be configured to have a maximum load-bearing capacity that is lower than the maximum load-bearing capacity of the repair loop 222 so that the sacrificial loop proactively breaks before the repair loop fails. For example, when the tissue graft 202 pulls in a direction away from the cortical button 210, in a direction D', the graft exerts a force on the distal end 406 of the repair loop 222 that causes the repair loop to stretch both distally and laterally. As the repair loop 222 is stretched laterally, the constricted side legs 416, 418 exert opposing forces against the transversely disposed sacrificial loop 502, thereby causing the sacrificial loop 502 to be stretched in opposite directions. Once the applied force exceeds the maximum load-bearing capacity of the sacrificial loop 502, the loop breaks and causes the patient to hear, feel or otherwise experience sensory feedback, e.g., a popping sound and/or an uneasy feeling or sensation, while the repair loop 222 remains intact. The earlier description of a threshold force is equally applicable to this embodiment, and all embodiments in which a maximum load-bearing capacity is discussed.

Further, in instances in which the sacrificial loop 502 includes a plurality of loops, the plurality of loops can have a variety of configurations, such as those described above with respect to the sacrificial loop 232 having multiple loops. For example, the plurality of loops can of the sacrificial loop can have similar threshold force values or they can have graduated threshold force values where different loops are configured to break under different values of force, thus providing for multiple warnings or triggers to be communicated to the subject based on the amount of force applied to the sacrificial loop 502.

Figure 6A:
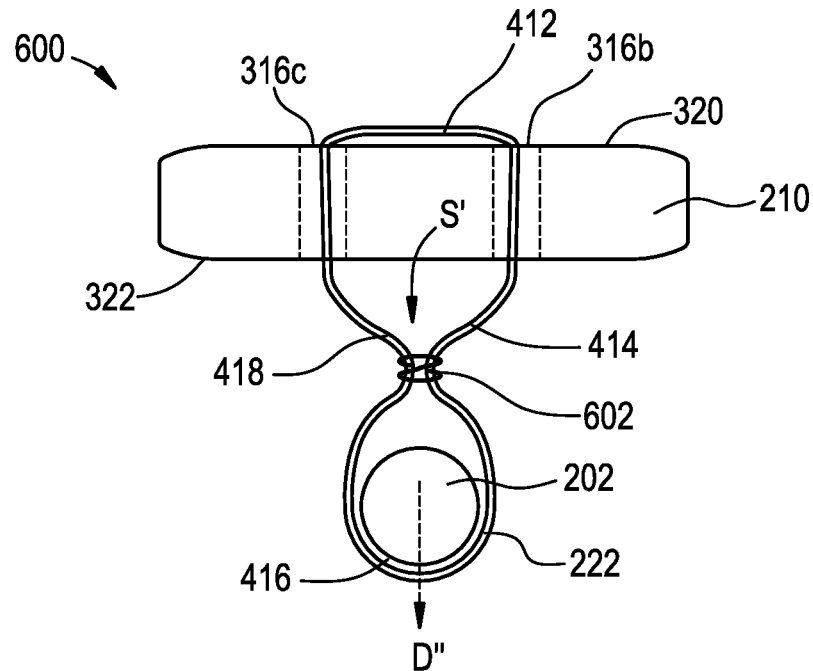
FIG. 6A illustrates a schematic cross-sectional side view of one exemplary embodiment of a surgical implant that includes a cortical button, a repair loop, and a sacrificial stitch between opposing side legs of the repair loop.
Figure 6B:
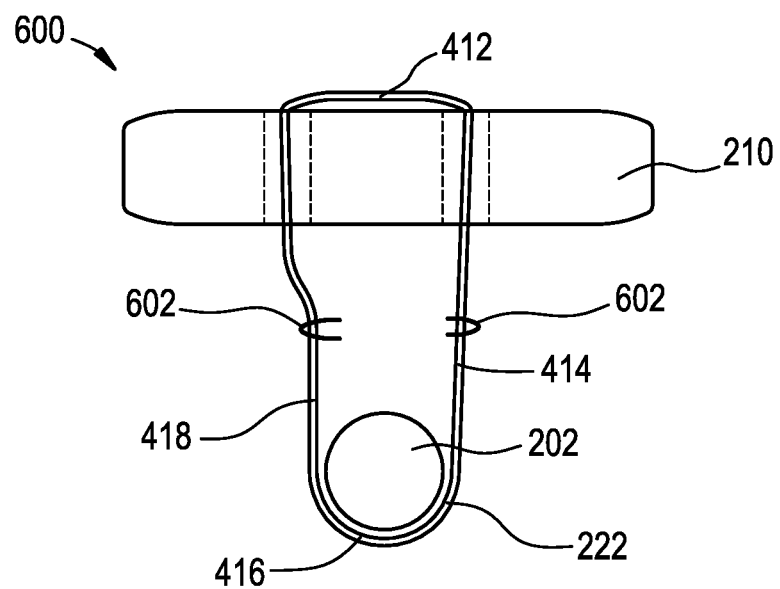
FIG. 6B illustrates a schematic cross-sectional side view of the surgical implant of FIG. 6A when the sacrificial stitch is broken.

Another non-limiting example of a sacrificial filament configuration is provided for in FIGS. 6A and 6B, in which the sacrificial filament includes a sacrificial stitch 602 associated with the repair loop 222. As shown, a surgical implant 600 includes the cortical button or body 210, the repair loop 222, and the sacrificial stitch 602 disposed in each of the opposing side legs 414, 418 of the repair loop 222. The surgical implant 600 is similar to the surgical implant 500 as shown and described above with respect to FIGS. 5A and 5B, however, the sacrificial filament is used to form the sacrificial stitch 602 to constrict the opposing side legs 414 and 418 of the repair loop 222 (instead of the transversely disposed sacrificial loop 502).

Similar to the sacrificial loop 502, the sacrificial stitch 602 can be associated with the repair loop 222 at a location between the bottom surface 322 of the cortical button 210 and a proximal surface of the tissue graft 202 captured with the repair loop 222. The sacrificial stitch 602 can include any number of stitches formed by the sacrificial filament, and thus references to a "stitch" is by no means limiting to a single stitch. In the illustrated embodiment, three stitches of the sacrificial stitch 602 are visible, but more or fewer, including as little as a single stitch, are possible. The number of stitches used can depend on a variety of factors, including but not limited to the desired strength of the sacrificial stitch 602 in comparison to the desired strength of the repair loop 222, the type of procedure in which the stitch 602 is being used, the anatomy and tendencies of the patient, and the preferences of the surgeon, among other factors.

The sacrificial stitch 602 can be formed in a variety of ways. By way of non-limiting example, the stitch may be passed through one of the opposing side legs 414, 418 just a single time before extending toward the other opposing side leg 414, 418 and passing through the other opposing side leg 414, 418 at least once. In other instances, the stitch may pass through one of the opposing side legs 414, 418 multiple times before extending toward the other opposing side leg 414, 418 and passing through the other opposing side leg 414, 418 at least once. In either instance, the stitch can, but does not have to, return back to the first opposing side leg for one or more additional stitches. In some instances, rather than passing the stitch(es) through the opposing side leg, they can be wrapped around the leg or otherwise associated with the legs using techniques known to those skilled in the surgical filament field.

No matter how the sacrificial stitch 602 is associated with the repair loop 222, the two can be associated in such a manner that a desired amount of constriction can be formed. This desired amount is similar to as described above with respect to the sacrificial loop 502, and thus it is understood it can result in various configurations, including instance in which the opposing side legs 414, 418 are touching at least one location and instances in which a space S' is disposed between the opposing side legs 414, 418, where the space S', sometimes referred to as a gap, is smaller than a space would exist between the side legs 414, 418 if no sacrificial element was associated with the repair loop 222.

The sacrificial stitch 602 can be configured to have a maximum load-bearing capacity that is lower than the maximum load-bearing capacity of the repair loop 222 so that the sacrificial stitch proactively breaks before the repair loop fails (the terminology surrounding the discussion of a threshold force above is equally applicable to this embodiment). For example, when the tissue graft 202 pulls in a direction away from the cortical button 210, in a direction D", the graft exerts a force on the distal end 406 of the repair loop 222 that causes the repair loop to stretch both distally and laterally. As the repair loop 222 stretches laterally, the constricted side legs 416, 418 exert opposing forces against the sacrificial stitch 602, and thereby causing the stitch to be stretched in opposite directions. Once the applied force exceeds the maximum load-bearing capacity of the sacrificial stitch 602, the stitch breaks and thereby causes the patient to hear, feel or otherwise experience sensory feedback, e.g., a popping sound and/or an uneasy feeling or sensation, while the repair loop 222 remains intact. Accordingly, as discussed above with reference to FIGS. 4A and 4B, the sensory feedback associated with the broken sacrificial stitch 602 can serve as warning to the patient to avoid certain movements or physical activity that can cause the tissue graft repair to fail.

Further, in instances in which the sacrificial stitch 602 includes multiple stitches, the stitches can be similar to the loops 232 and 502 that have multiple loops in that the stitches can be configured to have similar threshold force values or graduated threshold force values. In a graduated threshold force value configuration, different stitches of the sacrificial stitch 602 can have different threshold values such that different stitches break under different values of force applied to the sacrificial stitch 602.

Figure 7A:
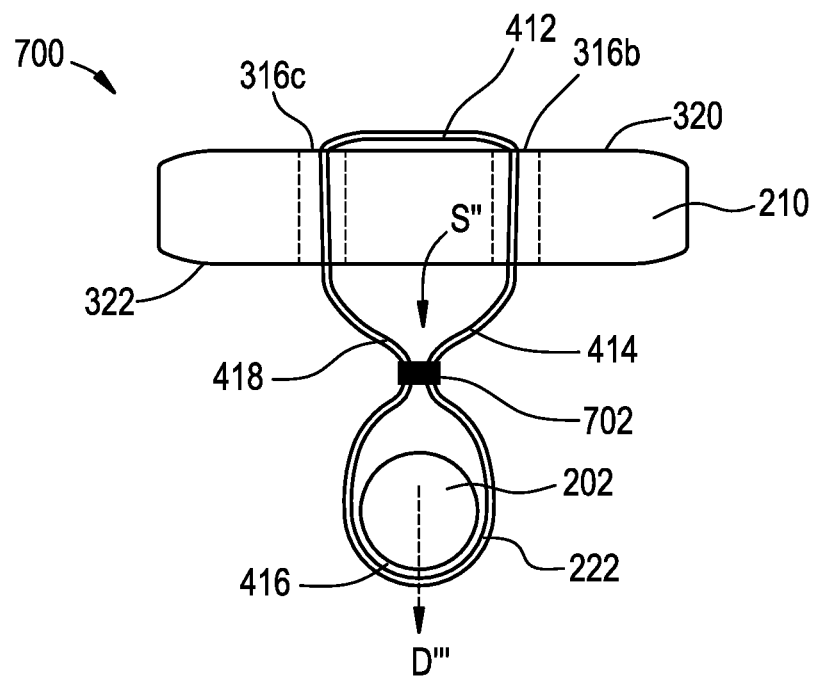
FIG. 7A illustrates a schematic cross-sectional side view of one exemplary embodiment of a surgical implant that includes a cortical button, a repair loop, and a sacrificial weld between opposing side legs of the repair loop.
Figure 7B:
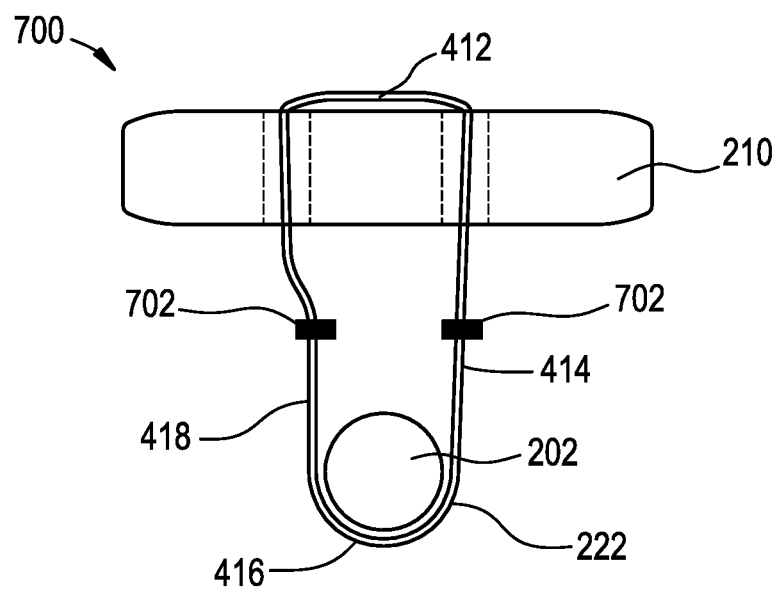
FIG. 7B illustrates a schematic cross-sectional side view of the surgical implant of FIG. 7A when the sacrificial weld is broken.

Yet another non-limiting example of a sacrificial filament configuration is provided for in FIGS. 7A and 7B, in which the sacrificial filament includes a sacrificial weld 702 associated with the repair loop 222. As shown, a surgical implant 700 includes the cortical button or body 210, the repair loop 222, and the sacrificial weld 702 associated with each of the opposing side legs 414, 418 of the repair loop 222. The surgical implant 700 is similar to the surgical implants 500, 600 as shown and described above with respect to FIGS. 5A and 5B and 6A and 6B, respectively, however, the sacrificial weld 702 constricts the opposing side legs 414 and 418 of the repair loop 222 (instead of the transversely disposed sacrificial loop 502 and the sacrificial stitch 602).

Similar to the sacrificial loop 502 and stitch 602, the sacrificial weld 702 can be associated with the repair loop 222 at a location between the bottom surface 322 of the cortical button 210 and a proximal surface of the tissue graft 202 captured with the repair loop 222. Further, although the illustrated embodiment illustrates a single weld, a person skilled in the art will appreciate multiple welds can be used, depending, at least in part, on factors such as the desired strength of the sacrificial weld 702 in comparison to the desired strength of the repair loop 222, the type of procedure in which the weld 702 is being used, the anatomy and tendencies of the patient, and the preferences of the surgeon, among other factors.

Similar to both the sacrificial loop 502 and the sacrificial stitch 602, the sacrificial weld 702 can be associated with the repair loop 222 at a location between the bottom side 322 of the cortical button 210 and a proximal surface of the tissue graft 202 captured within the repair loop 222. Further, a person skilled in the art will also understand various techniques that can be used to form one or more welds in conjunction with filament. By way of non-limiting example, a suture welding device that includes a heating element can be used to melt a portion of an outside component, such as another filament or other material, to constrict the opposing side legs 414, 418 of the repair loop 222. By way of further non-limiting example, a suture welding device that includes a heating element can be used to melt a portion of one or both of the opposing side legs 414, 418 of the repair loop 222 to the other leg.

No matter how the sacrificial weld 702 is associated with the repair loop 222, the two can be associated in such a manner that a desired amount of constriction can be formed. This desired amount is similar to as described above with respect to the sacrificial loop 502 and the sacrificial stitch 602, and thus it is understood it can result in various configurations having a designated amount of space S" therebetween, sometimes referred to as a gap, or no space or gap at all in some instances.

The sacrificial weld 702 can have a maximum load-bearing capacity that is lower than the maximum load-bearing capacity of the repair loop 222 so that the sacrificial weld can proactively break before the repair loop fails (the terminology surrounding the discussion of a threshold force above is equally applicable to this embodiment). For example, when the tissue graft 202 pulls in a direction away from the cortical button 210, in a direction D''', the graft exerts a force on the distal end 406 of the repair loop 222 that causes the repair loop to stretch both distally and laterally. As the repair loop 222 stretches laterally, the constricted side legs 416, 418 exert opposing forces against the sacrificial weld 702, and thereby cause the stitch to be stretched in opposite directions. Once the applied force exceeds the maximum load-bearing capacity of the sacrificial weld 702, the weld breaks and thereby causes the patient to hear, feel or otherwise experience sensory feedback, e.g., a popping sound and/or an uneasy feeling or sensation, while the repair loop 222 remains intact. Accordingly, as discussed above with reference to FIGS. 4A and 4B, the sensory feedback associated with the broken sacrificial weld 702 can serve as warning to the patient to avoid certain movements or physical activity that can cause the tissue graft repair to fail.

Further, in instances in which the sacrificial weld 702 includes a plurality of welds, the welds can be similar to the loops 232 and 502 and the stitch 602 that have multiple loops and stiches, respectively, in that the welds can be configured to have similar threshold force values or graduated threshold force values. In a graduated threshold force value configuration, different welds of the sacrificial weld 702 can have different threshold values such that different welds break under different values of force applied to the sacrificial weld 702.

Figure 8A:
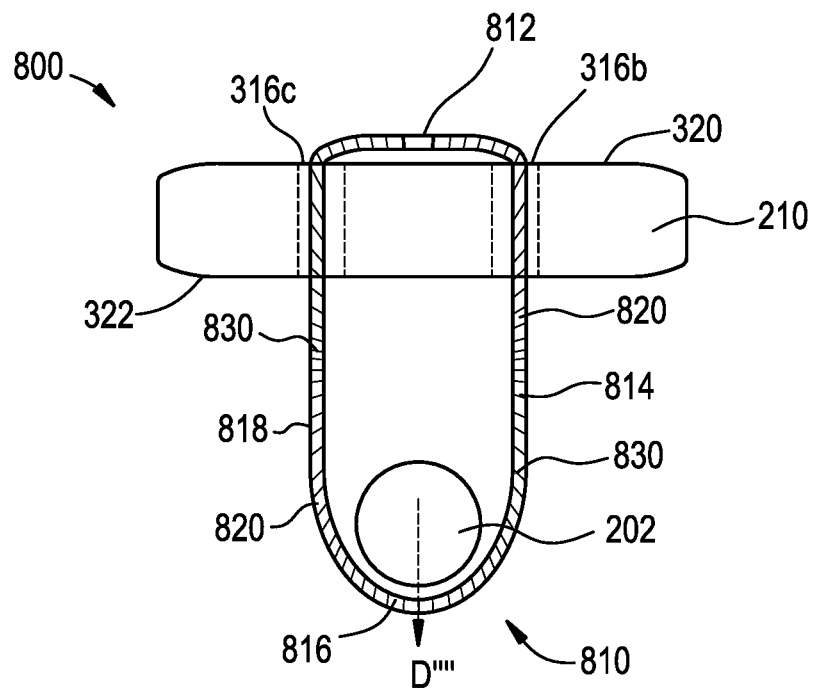
FIG. 8A illustrates a schematic cross-sectional side view of one exemplary embodiment of a surgical implant that includes a cortical button and an integrated repair loop formed by integrating a repair filament and a sacrificial filament.
Figure 8B:
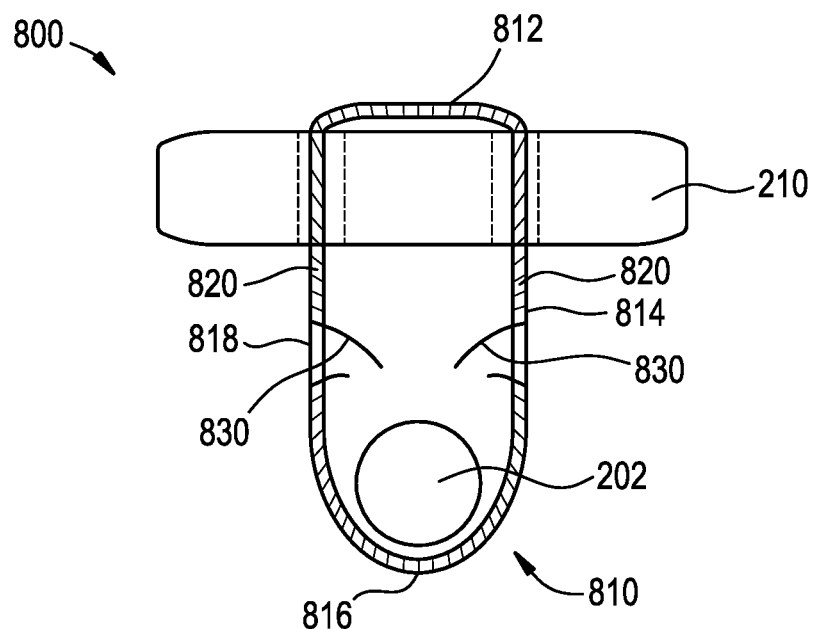
FIG. 8B illustrates a schematic cross-sectional side view of the surgical implant of FIG. 8A when the sacrificial filament of the integrated repair loop is broken.

Still another non-limiting example of a sacrificial filament configuration is provided for in FIGS. 8A and 8B, in which an operative filament 810 includes both a repair filament 820 and a sacrificial filament 830, with the sacrificial filament 830 being configured to proactively break before the repair filament 820. As shown, a surgical implant 800 includes a cortical button or body 210 and the operative filament 810 coupled thereto. More specifically, the operative filament 810 can include the repair filament 820 being associated or otherwise integrated with the sacrificial filament 830 to form an integrated repair loop (the operative filament 810 may also be referred to as the integrated repair loop 810, among other names in view of the way in which the repair and sacrificial filaments 820 and 830 are combined). A person skilled in the art, in view of the present disclosure, will understand a variety of ways by which the repair and sacrificial filaments 820 and 830 can be integrated, including but not limited to being intertwined, braided, woven, and wrapped with respect to each other, among other known manufacturing techniques. In the illustrated embodiment, the integrated repair loop 810 can include a proximal end 812 extending along a top surface 320 of the cortical button 210, a first side leg 814 extending from the top surface 320 through the first thru-hole 316b towards the tissue graft 202, a distal end 816 extending around a distal surface of the tissue graft 202, and a second side leg 818 extending from the tissue graft 202 to the bottom surface 322 of the button and through the second thru-hole 316c to complete the loop. Further, although in the illustrated embodiment the integrated repair loop 810 includes a single repair filament 820 and a single sacrificial filament 830, a person skilled in the art will recognize multiple repair filaments and/or sacrificial filaments can be formed into the integrated repair loop 810 such that there are multiple integrated repair filaments and/or sacrificial filaments.

The sacrificial filament 830 can be configured to have a lower maximum load-bearing capacity than the repair filament 820 so that the sacrificial filament of the integrated repair loop 810 proactively breaks before the repair filament of the loop 810 fails (the terminology surrounding the discussion of a threshold force above is equally applicable to this embodiment). For example, when the tissue graft 202 pulls in a direction away from the cortical button 210, in a direction D″, the graft exerts a force on the distal end 816 of the integrated repair loop 810 that causes the loop to stretch. Once the applied force of the tissue graft 202 exceeds the maximum load-bearing capacity of the sacrificial filament 830, the sacrificial filament breaks and thereby causing the patient to hear, feel or otherwise experience sensory feedback, e.g., a popping sound and/or an uneasy feeling or sensation. Because the sacrificial filament 830 is configured to break at loads that do not break the repair filament 820, the sacrificial filament 830 can break while the repair filament 820 of the integrated repair loop 810 remains intact and thereby maintains the attachment between the cortical button 210 and the tissue graft 202.

As previously discussed with reference to FIGS. 4A and 4B, the sacrificial filament 830 can be configured to have a lower maximum load-bearing capacity than the repair filament 820 using a variety of techniques. These techniques may include, but are not limited to, using a filament material for the sacrificial filament 830 having a modulus of elasticity that is less than the modulus of elasticity of the repair filament 820, using a filament material for the sacrificial filament 830 having a diameter or thickness that is smaller than the diameter or thickness of the repair filament 820, and/or using a filament material for the sacrificial filament 830 having a different configuration than the repair filament 820 (e.g., the repair filament 820 is integrated more tightly than the sacrificial filament 830, the repair filament 820 is integrated and the sacrificial filament 830 is not).

In some embodiments of the variously illustrated implants 400, 500, 600, 700, and 800 of FIGS. 4A-8B, the maximum load-bearing capacity of the sacrificial filament 830 can be about approximately one half of the maximum load-bearing capacity of the repair filament 220, 820. For example, for anterior or posterior cruciate ligament repairs, the maximum load-bearing capacity of the sacrificial filament 230, 502, 602, 702, 830 can be approximately in the range of about 100 Newtons (N) to about 1000 N, and in some embodiments it can be about 250 N, and the maximum load-bearing capacity of the repair filament 220, 820 can be approximately in the range of about 1000 N to about 2500 N, and in some embodiments it can be about 1500 N. Alternatively, in some embodiments the maximum load-bearing capacity of the sacrificial filament 230, 502, 602, 702, 830 can be less than one half of the maximum load-bearing capacity of the repair filament 220, 820, while in still other embodiments the maximum load-bearing capacity of the sacrificial filament 230, 502, 602, 702, 830 can be more than one half but less than the maximum load-bearing capacity of the repair filament 220, 820.

Figure 9A:
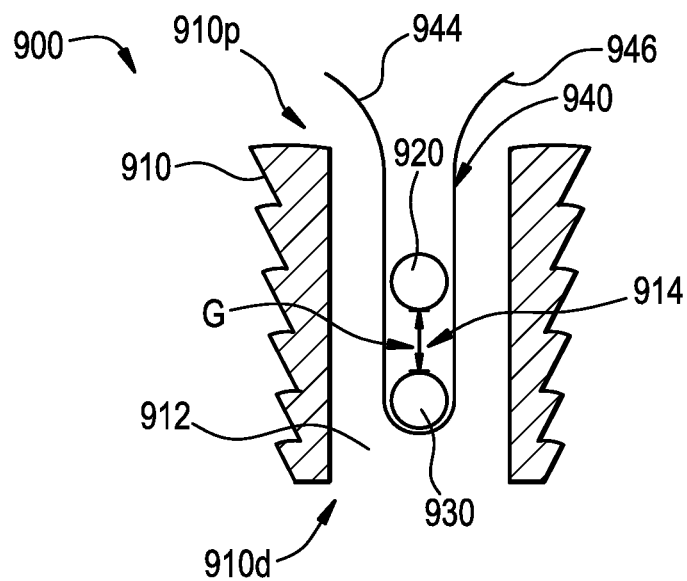
FIG. 9A illustrates a schematic cross-sectional side view of one exemplary embodiment of a surgical implant that includes a suture anchor having a filament engagement mechanism and a sacrificial filament engagement mechanism.
Figure 9B:
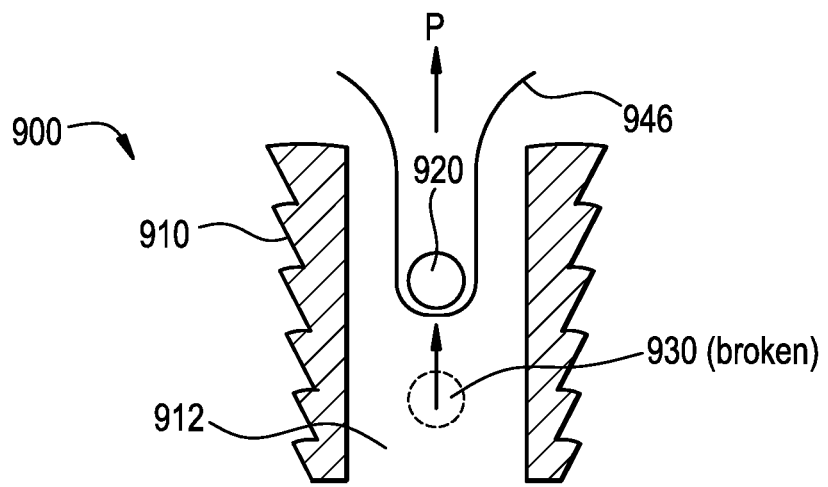
FIG. 9B illustrates a schematic cross-sectional side view of the surgical implant of FIG. 9A when the sacrificial filament engagement mechanism is broken.

The present disclosure also provides for sacrificial elements that are part of the implantable body itself. By way of example, FIGS. 9A and 9B illustrate a surgical implant 900 that includes a suture or bone anchor 910 having both a filament engagement mechanism 920 and a sacrificial filament engagement mechanism 930. While the illustrated embodiment only provides for a cross-sectional view of the anchor, a person skilled in the art will understand many different types of suture anchors and configurations that can be representative of, or adapted in view of, the illustrated embodiment. The anchor 910 can be engaged by a repair filament 940, which as shown in FIG. 9 can start by being engaged to the sacrificial filament engagement mechanism 930. The repair filament 940 can be used in a variety of tissue repair techniques, and may or may not involve the use of a graft. As described further below, the implant 900 can be configured such that the sacrificial filament engagement mechanism 930 breaks or otherwise allows the repair filament 940 to move to the filament engagement mechanism 920 when a threshold force value is exceeded.

In the illustrated embodiment of FIG. 9A, the suture anchor 910 includes an axial bore or passageway 912 formed therethrough from a proximal end 910p to a distal end 910d. In other embodiments, the bore may only be partially formed therethrough. The filament engagement mechanisms 920 and 930 can be transversely disposed across the axial bore 912 such that the sacrificial filament engagement mechanism 930 is spaced distally below and apart from the filament engagement mechanism 920. In some embodiments, the space or gap G 914 between the filament engagement mechanisms 920 and 930 can be approximately in a range from about 0.1 mm to about 1 mm.

In some embodiments, one or both filament engagement mechanisms 920, 930 can be a post, saddle, crossbar, shaft, rod, spoke, or other rigid structure for coupling a filament to a suture anchor. Such mechanisms 920, 930 can be integrally formed parts or components of a suture anchor, or, alternatively, one or both mechanisms 920, 930 can be separate parts or components that are designed to be connected, attached, fixed, or otherwise coupled to a suture anchor. A person skilled in the art will understand many different types of filament engagement mechanisms that can be used as part of a suture anchor, whether integrally or separately formed, and thus the present illustrations and descriptions are by no means limiting. Further, although in the illustrated embodiment the filament engagement mechanisms 920 and 930 are of a similar type, they can be different types, configurations, sizes, shapes, etc.

In the illustrated embodiment, the repair filament 940 is slidably attached to the anchor 910 by extending the repair filament 940 into the axial bore 912 and around the sacrificial filament engagement mechanism 930. With the sacrificial filament engagement mechanism 930 intact, the distal end 942 of the repair filament 940 is spaced apart from the filament engagement mechanism 920 by the distance of the gap G. The terminal ends 944 and 946 of the repair filament 940 can be manipulated in a number of different ways known to those skilled in the art to secure soft tissue (or possibly a graft) to bone, including but not limited to the teachings of U.S. Pat. Nos. 8,814,905, 8,821,543, 8,894,684, 9,095,331, 9,060,763, 9,345,468, 9,763,655 and U.S. Patent Application Publication No. 2017/0215864, the contents of each which is incorporated by reference herein in its entirety.

The sacrificial filament engagement mechanism 930 can be configured to have a maximum load-bearing capacity that is lower than the maximum load-bearing capacity of the filament engagement mechanism 920. The respective load-bearing capacities of the filament engagement mechanisms 920 and 930 can be defined as the maximum stress (e.g., force) or strain (e.g., deformation) that the filament engagement mechanism can stand without breaking or otherwise failing. For example, when the repair filament 940 exerts a force on the filament engagement mechanism 930 in a direction P, towards the filament engagement mechanism 920, the distal end 942 of the repair filament 940 exerts a force on the sacrificial filament engagement mechanism 930. Once the applied force of the repair filament 940 exceeds the maximum load-bearing capacity of the sacrificial filament engagement mechanism 930, the sacrificial filament engagement mechanism 930 breaks or otherwise fails such that the sacrificial filament engagement mechanism 930 can no longer support the repair filament 940, thus releasing the repair filament 940. This can also be referred to as a threshold force, which is the minimum amount of force that can be applied to the sacrificial filament engagement mechanism to cause it to break. Forces greater than the threshold force may also cause the sacrificial filament engagement mechanism to break, while forces less than the threshold force are not, at least alone, large enough to cause the sacrificial filament engagement mechanism to break. Once the sacrificial filament engagement mechanism breaks, the application of the force in the direction P can cause the repair filament 940 to be engaged or otherwise captured by the filament engagement mechanism 920, which can subsequently maintain a location of the repair filament 940 with respect to the anchor 910 because its threshold value, or maximum load-bearing capacity, exceeds that of the sacrificial filament engagement mechanism 930.

A person skilled in the art will recognize there are a number of different ways by which the sacrificial filament engagement mechanism 930 and the filament engagement mechanism 920 can be constructed so that they have different load-bearing capacities. In some embodiments, the sacrificial filament engagement mechanism 930 can be configured to have a lower maximum load-bearing capacity by using a material having a modulus of elasticity that is less than the modulus of elasticity of the filament engagement mechanism 920. Additionally or alternatively, the sacrificial filament engagement mechanism 930 can be configured to have a lower maximum load-bearing capacity by using reducing the diameter or thickness of the sacrificial filament engagement mechanism 930 to be smaller than the diameter or thickness of the filament engagement mechanism 920. By way of further non-limiting example, the sacrificial filament engagement mechanism 930 can include one or more preformed breaking points manufactured or otherwise formed therein than allow it to break when a certain threshold force is applied to it. Other ways of making the two filament engagement mechanism 920 and 930 have different threshold values for load-bearing are derivable in view of the present disclosures and knowledge of a person skilled in the art, and thus such incorporation of the techniques is within the spirit of the present disclosure.

In some embodiments, the maximum load-bearing capacity of the sacrificial filament engagement mechanism 930 can be about approximately one half of the maximum load-bearing capacity of the filament engagement mechanism 920. For example, for rotator cuff repairs, the maximum load-bearing capacity of the sacrificial filament engagement mechanism 930 can be approximately in the range of about 50 Newtons (N) to about 500 N, and in some embodiments it can be about 150 N, and the maximum load-bearing capacity of the filament engagement mechanism 920 can be approximately in the range of about 100 N to about 1000 N, and in some embodiments it can be about 300 N. Alternatively, in some embodiments, the maximum load-bearing capacity of the sacrificial filament engagement mechanism 930 can be less than one half of the maximum load-bearing capacity of the filament engagement mechanism 920, while in still other embodiments the maximum load-bearing capacity of the sacrificial filament engagement mechanism 930 can be more than one half but less than the maximum load-bearing capacity of the filament engagement mechanism 920.

When the sacrificial filament engagement mechanism 930 breaks, the patient may hear, feel, or otherwise experience some form of sensory feedback. For example, in some embodiments, the sensory feedback may be a sound (e.g., a popping sound) of the sacrificial filament engagement mechanism 930 breaking. In some embodiments, the patient may feel a slight movement of the repair filament 940 in response to the distal end 942 of the repair filament 940 being released from the sacrificial filament engagement mechanism 930 until captured by the filament engagement mechanism 920. Thus, the sensory feedback associated with the sacrificial filament engagement mechanism 930 breaking can serve as a warning that the patient's physical activity or movements may risk failure of the tissue graft repair. The warning may also cause patients to seek out medical attention or advice.

A person skilled in the art will appreciate that the various sacrificial elements provided for herein can be used in conjunction with each other. For example, both a sacrificial filament (e.g., the sacrificial elements 230, 502, 602, 702, 830) and a sacrificial engagement mechanism (e.g., the sacrificial engagement mechanism 930) can both be incorporated with or otherwise used in conjunction with a single implant. Likewise, more than one configuration of a sacrificial filament (e.g., the sacrificial elements 230, 502, 602, 702, 830) can be used together in the same implant. In either or both instances, such a design can provide additional fail-safes that break at approximately the same threshold value of force, and/or they can be designed in a tiered configuration as provided for above, in which one sacrificial element is designed to fail at a first threshold value of force and another sacrificial element is designed to fail at a second threshold value of force that is greater than the first threshold value of force.

While a variety of uses are provided for above either in discussing the various embodiments or in the various patents and patent applications incorporated by reference, two general descriptions of a use of a surgical implant that includes a sacrificial element are provided below. The first describes a procedure involving an implant having at least one sacrificial filament associated therewith for use in conjunction with a graft, and the second describes a procedure involving an implant having at least one sacrificial engagement mechanism that is part of a body of the implant for use in conjunction with repairing tissue. Because the general surgical techniques for implanting a graft and repairing a tissue are known, illustrations of the same are unnecessary. The enhancements to these procedures will be evident from the disclosures herein.

In one use, the implant is the implant 200 having an implant body 210, a repair filament 220, and a sacrificial filament 230, as shown in FIG. 4A. A person skilled in the art will recognize these descriptions of use can be applied without much difficulty to the other configurations provided for herein (e.g., the implants 500, 600, and 700) or otherwise derivable from the present disclosures. To start, desired tunnels and bores can be formed at the surgical site to provide a location at which a graft 202 will be disposed. The tunnels and bores formed will depend, at least in part, on the type of procedure being performed. Some exemplary procedures can include ligament repair procedures, such as cruciate ligament procedures using a ligament graft(s) (e.g., ACL and MCL procedures). In some embodiments, at least one bone tunnel in at least one bone can be formed. The implant 200 can be implanted with respect to the bone tunnel such that the implant body 210 rests against the bone proximate to one end of the bone tunnel and the repair filament 220 and the sacrificial filament 230 extend away from the implant body 210 and into the bone tunnel. In some instances the implant body 210 can be passed into and through the bone tunnel, beginning at the opposite end from where it rests against the bone, while in other instances the implant body can be positioned at its resting location with the filaments 220 and 230 being manipulated into the bone tunnel.

A graft 202 can be coupled to the implant 200 by associating the graft 202 with the sacrificial filament 230. The association can occur prior to, during, or after the body 210 is passed into the bone tunnel. By way of non-limiting example, in instances in which the implant body 210 is passed into and through the bone tunnel, the graft 202 can be associated or otherwise coupled to the sacrificial element 230 prior to positioning the implant body at the opposite end where it rests such that the sacrificial element 230 and graft 202 are passed through at least a portion of the bone tunnel while associated with each other. The association of the sacrificial element 230 and graft 202 can be achieved in a variety of manners. By way of non-limiting examples, a portion of the graft 202 can be passed through an opening of the loop 232 formed by the sacrificial filament 230 and/or a portion of the sacrificial filament 230 can be passed through the graft 202 itself. The rest of the surgery can be performed to position the graft at the desired location with respect to the bone and the bone tunnel. Any openings formed in the body to perform the procedure can be closed, with the net result being the implant 200 holding the graft 202 by way of the sacrificial filament 230 in the bone tunnel and the repair filament 220 being disposed some distance away from graft 202, as illustrated the distance H in FIG. 4A, the repair filament 220 also being disposed in the bone tunnel.

Following the completion of the procedure, if a movement is made by the patient that causes a force applied to sacrificial element 230 by the graft 202 to exceed the threshold force of the sacrificial element 230, the sacrificial element 230 is configured to break, as shown in FIG. 4B. This results in the graft 202 being let loose and traveling the distance H until it engages the repair filament 220. The repair filament 220 can catch and hold the graft 202, thus maintaining the integrity of the procedure. The distance H can be such that the movement for that length does not cause any serious ramifications to the patient due to the movement of the graft 202 that amount. As discussed above, the breaking of the sacrificial element 230 can cause some sort of signal to the patient (e.g., auditory, feeling, etc.) to let the patient know the movement that resulted in the breaking of the sacrificial element 230 was not desirable and should be avoided in the future. The patient can also use this signal to notify the appropriate medical provider so any other recommended actions can be carried out or conveyed to the patient.

In another use, the implant is the implant 900 having a suture anchor 910, a filament engagement mechanism 920, a sacrificial filament engagement mechanism 930, and a repair filament 940, as shown in FIG. 9A. To start, desired bone holes or tunnels can be formed at the surgical site to provide a location at which the suture anchor 910 will be disposed. The bores and tunnels formed will depend, at least in part, on the type of procedure being performed. Some exemplary procedures can include tissue repair procedures to repair complete or partial detachments of tendons, ligaments, and other soft tissues from bones, such as for rotator cuffs and Achilles tendons. In some embodiments, at least one bone bore is formed in the bone, the bore being designed to receive the suture anchor 910. The implant 900 can be implanted with respect to the bone bore using any technique known for inserting a suture anchor 910 into a bone bore, including a suture anchor inserter that pushes and/or rotates the anchor 910 to a desired location within the bore.

The repair filament 940 can extend from the anchor 910, away from the bone and its bore. The repair filament can be coupled to the anchor 910 by way of the sacrificial filament engagement mechanism 930. The association can occur prior to, during, or after the anchor 910 is passed into the bone bore. Thus, in some instances the repair filament 940 may be disposed around at least a portion of the sacrificial filament engagement mechanism 930 prior to disposing the anchor 910 in the bore, while in other instances the repair filament 940 may be disposed around at least a portion of the sacrificial filament engagement mechanism 930 after the anchor 910 has been disposed in the bore.

Once the anchor 910 and repair filament 940 are located in their desired locations, the remainder of the procedure can be performed. This can include manipulating the repair filament 940 or associated tissue to eventually draw the tissue towards the bone in which the anchor 910 is implanted. Alternatively, the location at which the tissue is to be disposed can be a location that is not the bone in which the anchor 910 is implanted. For example, the anchor 910 could be disposed in a bone proximate to the desired location of the tissue because the bone in which the anchor 910 is disposed provides for a more stable environment for the anchor 910 than the bone at which the tissue is to be disposed. The purpose of the present disclosure, nevertheless, is achieved even if the bone in which the anchor 910 is disposed is different than the bone to which the tissue is to be drawn. Any techniques for drawing tissue to bone using filament can be used. Once the rest of the surgery is completed, any openings formed in the body to perform the procedure can be closed, with the net result being the anchor 910 holding the repair filament 940 by way of the sacrificial filament engagement mechanism 930 and the repair filament 940 holding the location of tissue being repaired at a desired location with respect to bone. The filament engagement mechanism 920 is disposed at a location more proximate to the tissue than the sacrificial filament engagement mechanism 930 is located, as illustrated by the distance G in FIG. 9A.

Following the completion of the procedure, if a movement is made by the patient that causes a force applied to sacrificial filament engagement mechanism 930 by the repair filament 940 to exceed the threshold force of the sacrificial filament engagement mechanism 930, the sacrificial filament engagement mechanism 930 is configured to break, as shown in FIG. 9B. This results in the repair filament 940 being let loose and traveling the distance G until it engages the filament engagement mechanism 920. The filament engagement mechanism 920 can catch and hold the repair filament 940, thus maintaining the integrity of the procedure. The distance G can be such that the movement for that length does not cause any serious ramifications to the patient due to the movement of the repair filament 940, and thus possibly the associated tissue, that amount. As discussed above, the breaking of the sacrificial filament engagement mechanism 930 can cause some sort of signal to the patient (e.g., auditory, feeling, etc.) to let the patient know the movement that resulted in the breaking of the sacrificial filament engagement mechanism 930 was not desirable and should be avoided in the future. The patient can also use this signal to notify the appropriate medical provider so any other recommended actions can be carried out or conveyed to the patient.

One skilled in the art will appreciate further features and advantages of the disclosure based on the above-described embodiments. Accordingly, the disclosure is not to be limited by what has been particularly shown and described, except as indicated by the appended claims. For example, to the extent the present disclosure disclose using the devices and methods provided for herein for soft tissue repairs associated with the knee and shoulder, a person skilled in the art will recognize how the present disclosures can be adapted for use with other anatomies. All publications and references cited herein are expressly incorporated herein by reference in their entirety.

What is claimed is:

1. A surgical implant, comprising:
   an implantable body having a top side, an opposed bottom side, and at least two passageways extending at least partially therethrough, each passageway extending between a proximal end and a distal end of the implantable body;
   a repair filament disposed in the at least one passageway of the implantable body, the repair filament forming a repair loop configured to connect the implantable body and a tissue, the repair filament having a first maximum load-bearing capacity; and
   a sacrificial element associated with at least one of the implantable body or the repair filament, the sacrificial element comprising a sacrificial filament and the sacrificial element being configured to carry an applied load of at least one of the repair filament or the tissue, the sacrificial element having a second maximum load-bearing capacity that is lower than the first maximum load-bearing capacity of the repair filament such that the sacrificial element is configured to produce sensory feedback in response to the applied load of the at least one of the repair filament or the tissue exceeding the second maximum load-bearing capacity,
   wherein each of the repair filament and the sacrificial filament extend through each of the at least two passageways such that each of the repair filament and the sacrificial filament is disposed above the top side of the implantable body and below the bottom side of the implantable body, and
   wherein the sacrificial filament forms a sacrificial loop configured to produce the sensory feedback in response to an applied load from the tissue when the applied load exceeds the second maximum load-bearing capacity of the sacrificial filament.

2. The surgical implant of claim 1, wherein the sensory feedback is associated with the sacrificial loop breaking in response to the applied load from the tissue when the applied load exceeds the second maximum load-bearing capacity of the sacrificial filament.

3. The surgical implant of claim 1, wherein a circumference formed by the sacrificial loop is smaller than a circumference formed by the repair loop.

4. The surgical implant of claim 1, wherein the second maximum load-bearing capacity of the sacrificial filament is approximately one half of the first maximum load-bearing capacity of the repair filament.

* * * * *